United States Patent
Choi et al.

(10) Patent No.: US 11,674,184 B2
(45) Date of Patent: Jun. 13, 2023

(54) ENHANCING RADIATION SENSITIVITY COMPRISING ADMINISTERING PMVK INHIBITING SIRNA AND SHRNA

(71) Applicant: ENHANCEDBIO INC., Seoul (KR)

(72) Inventors: Eun Kyung Choi, Seoul (KR); Seong-Yun Jeong, Yongin-si (KR); Si Yeol Song, Seoul (KR); Yun-Yong Park, Seoul (KR); Seok Soon Park, Bucheon-si (KR); Eun Jin Ju, Seoul (KR); Eun Jung Ko, Seoul (KR)

(73) Assignee: ENHANCEDBIO INC., Seoul (KR)

( * ) Notice: Subject to any disclaimer, the term of this patent is extended or adjusted under 35 U.S.C. 154(b) by 232 days.

(21) Appl. No.: 16/766,297

(22) PCT Filed: Nov. 21, 2018

(86) PCT No.: PCT/KR2018/014363
§ 371 (c)(1),
(2) Date: May 22, 2020

(87) PCT Pub. No.: WO2019/103456
PCT Pub. Date: May 31, 2019

(65) Prior Publication Data
US 2021/0025007 A1   Jan. 28, 2021

(30) Foreign Application Priority Data

Nov. 22, 2017 (KR) .......................... 10-2017-0156320
Nov. 20, 2018 (KR) .......................... 10-2018-0143493

(51) Int. Cl.
| | | |
|---|---|---|
| *A61K 38/55* | (2006.01) | |
| *A61K 31/7105* | (2006.01) | |
| *A61P 35/00* | (2006.01) | |
| *C12N 15/113* | (2010.01) | |
| *C12Q 1/6886* | (2018.01) | |
| *A61K 38/00* | (2006.01) | |

(52) U.S. Cl.
CPC ........ *C12Q 1/6886* (2013.01); *A61K 31/7105* (2013.01); *A61K 38/005* (2013.01); *A61K 38/55* (2013.01); *A61P 35/00* (2018.01); *C12N 15/1137* (2013.01); *C12N 2310/14* (2013.01); *C12Y 207/04002* (2013.01)

(58) Field of Classification Search
None
See application file for complete search history.

(56) References Cited

U.S. PATENT DOCUMENTS

| | | |
|---|---|---|
| 7,939,263 B2 | 5/2011 | Clarke et al. |
| 2010/0048414 A1 | 2/2010 | Weaver et al. |
| 2011/0129822 A1 | 6/2011 | Shen et al. |
| 2014/0363816 A1 | 12/2014 | Theodorescu et al. |
| 2016/0313302 A1 | 10/2016 | DeBrabander et al. |
| 2017/0253933 A1 | 9/2017 | Wang |

FOREIGN PATENT DOCUMENTS

| | | | | |
|---|---|---|---|---|
| CA | 3072087 | * | 2/2019 | ............ A61K 31/00 |
| JP | 2013-511999 A | | 4/2013 | |
| JP | 2016-521966 A | | 7/2016 | |
| KR | 10-2017-0094165 A | | 8/2017 | |
| WO | 2005067391 A2 | | 7/2005 | |
| WO | WO 2012/048303 | * | 4/2012 | ............... C12Q 1/68 |
| WO | 2017104912 A1 | | 6/2017 | |

OTHER PUBLICATIONS

Partial schematic downloaded Oct. 14, 2022 from https://commons.wikimedia.org/w/index.php?curid=21786963 and reproduced in action. (Year: 2022).*
Hu et al., Signal Transduction and Targeted Therapy (2020) 5:101 (Year: 2020).*
Piche-Nicholas et al., MAbs. 2018; 10: 81-94. doi: 10.1080/19420862.2017.1389355 (Year: 2018).*
Efimova et al., Mol Cancer Ther; 17(2), 407-418 (Year: 2017).*
Cho, International Journal of Oncology, 2015; 46: 1149-1158 (Year: 2015).*
Samuel A. Hasson et al., "Chemogenomic Profiling of Endogenous PARK2 Expression Using a Genome-Edited Coincidence Reporter", ACS Chemical Biology, 2015, vol. 10, No. 5, Feb. 26, 2015, pp. 1188-1197.
Pornthip Boonsri et al., "Molecular Docking and NMR Binding Studies to Identify Novel Inhibitors of Human Phosphomevalonate Kinase", Biochemical and Biophysical Research Communications, vol. 430, Issue 1, Jan. 4, 2013, pp. 313-319.
International Search Report for PCT/KR2018/014363 dated Apr. 30, 2019 from Korean Intellectual Property Office.
Lloyd, Katherine L et al., "Prediction of resistance to chemotherapy in ovarian cancer: a systematic review", BMC Cancer. 2015, vol. 15, Article No. 117, pp. 1-32.
Bisrat G. Debeb et al., "Radiation Resistance of Breast Cancer Stem Cells: Understanding the Clinical Framework", J Mammary Gland Biol Neoplasia (2009) 14:11-17.

(Continued)

*Primary Examiner* — Christina M Borgeest
(74) *Attorney, Agent, or Firm* — Revolution IP, PLLC (57) ABSTRACT

The present invention relates to a biomarker composition for diagnosing radiation-resistant cancer comprising PMVK as an active ingredient and a method of diagnosing radiation-resistant cancer using the same, and when the PMVK is knocked down, it is confirmed that the survival rate of cancer cells decreases during radiation treatment, and based on this, the possibility as a factor related to radiation therapy resistance to cancer was suggested, and the PMVK can be used as a new target to enhance the effect of radiation therapy on human cancer cells.

2 Claims, 7 Drawing Sheets

Specification includes a Sequence Listing.

(56) References Cited

OTHER PUBLICATIONS

Ki-Tae Hwang et al., "Genomic copy number alterations as predictive markers of systemic recurrence in breast cancer", Int. J. Cancer: 123, 1807-1815 (2008).
Xian-Hui Long et al., "Dose-dependent expression changes of eariy response genes to ionizing radiation in human lymphoblastoid cells", International Journal of Molecular Medicine 19: 607-615, 2007.

* cited by examiner

ENHANCING RADIATION SENSITIVITY COMPRISING ADMINISTERING PMVK INHIBITING SIRNA AND SHRNA

CROSS REFERENCE TO PRIOR APPLICATIONS

This application is a National Stage Application of PCT International Patent Application No. PCT/KR2018/014363 filed on Nov. 21, 2018, under 35 U.S.C. § 371, which claims priority to Korean Patent Application Nos. 10-2017-0156320 filed on Nov. 22, 2017 and 10-2018-0143493 filed on Nov. 20, 2018, which are all hereby incorporated by reference in their entirety.

TECHNICAL FIELD

The present invention relates to a biomarker composition for diagnosing radiation-resistant cancer comprising a phosphomevalonate kinase (PMVK) protein or a gene encoding the same as an active ingredient, and a method of diagnosing radiation-resistant cancer using the same. In addition, the present invention relates to a biomarker composition for predicting prognosis of radiation therapy in a cancer patient comprising a PMVK and a method of predicting prognosis of radiation therapy in a cancer patient using the same.

BACKGROUND ART

Cancer treatment methods include surgical surgery, chemical drug therapy and radiation therapy and recently, the importance of radiation therapy has increased. In cases where surgical surgery is difficult, cases have been reported to effectively cure tumors only with radiation therapy, and methods of treating tumors using radiation have been progressing over the years, and radiation therapy has established itself as an efficient treatment of tumors in the body without special pain or refusal to the patient.

However, acquisition of radiation resistance of cancer cells and damaging normal tissues during high-dose radiation treatment have been pointed out as problems that reduce the efficiency of radiation treatment, and thus, a study on radiation therapy sensitizers to improve the efficiency of radiation treatment is necessary. The radiation therapy sensitizers reported to date is mainly anticancer drugs, for example, taxol and cisplatin have been reported to be used as a radiation therapy sensitizer in solid cancers such as breast cancer, uterine cancer, lung cancer, stomach cancer and colon cancer. However, these radiation treatment sensitizers themselves are substances used as anticancer agents, and thus have high side effects to have a problem of their limited use.

Therefore, beyond the limitations of these conventional radiation therapy sensitizers, it is necessary to study molecular signals to increase the sensitivity to radiation-resistant cells as well as to predict radiation therapy results.

DISCLOSURE

Technical Problem

It is an object of the present invention is to provide a biomarker composition for diagnosing radiation-resistant cancer comprising a PMVK as an active ingredient and a composition for diagnosing radiation-resistant cancer comprising an agent capable of measuring expression level of PMVK as an active ingredient.

It is another object of the present invention is to provide a biomarker composition for predicting the prognosis of radiation therapy in a cancer patient comprising PMVK as an active ingredient and a composition for predicting the prognosis of radiation therapy in a cancer patient comprising an agent capable of measuring the expression level of PMVK as an active ingredient.

It is another object of the present invention is to provide a pharmaceutical composition for enhancing radiation sensitivity to cancer cells comprising a PMVK protein expression inhibitor or activity inhibitor as an active ingredient.

It is another object of the present invention is to provide a method of diagnosing radiation-resistant cancer using the expression and activity level of PMVK protein and a method of predicting the prognosis of radiation therapy in a cancer patient.

It is another object of the present invention is to provide a method of screening a radiation sensitivity enhancer for cancer cells by measuring the expression level of a PMVK protein.

It is another object of the present invention is to provide a use of a PMVK protein or a gene encoding the same, as a biomarker for diagnosing radiation-resistant cancer.

It is another object of the present invention is to provide a use of an agent capable of measuring the expression level of PMVK for diagnosing radiation-resistant cancer.

It is another object of the present invention is to provide a use of a PMVK protein or a gene encoding the same, as a biomarker for predicting the prognosis of radiation therapy in a cancer patient.

It is another object of the present invention is to provide a use of an agent capable of measuring the expression level of a PMVK for predicting the prognosis of radiation therapy in a cancer patient.

It is another object of the present invention is to provide a use of a PMVK protein expression or activity inhibitor for the manufacture of a medicament for enhancing the radiation sensitivity to cancer cells.

Technical Solution

In order to achieve the above object, the present invention provides a biomarker composition for diagnosing radiation-resistant cancer comprising a phosphomevalonate kinase (PMVK) protein or a gene encoding the same as an active ingredient.

Also, the present invention provides a composition for diagnosing radiation-resistant cancer comprising an agent capable of measuring expression level of PMVK as an active ingredient and a kit for diagnosing radiation-resistant cancer comprising the same.

In order to achieve the another object, the present invention provides a biomarker composition for predicting the prognosis of radiation therapy in a cancer patient comprising a phosphomevalonate kinase (PMVK) protein or a gene encoding the same as an active ingredient.

In addition, the present invention provides a composition for predicting the prognosis of radiation therapy in a cancer patient comprising an agent capable of measuring the expression level of PMVK as an active ingredient and a kit for predicting the prognosis of radiation therapy in a cancer patient comprising the same.

In order to achieve the above another object, the present invention provides a pharmaceutical composition for promoting the radiation sensitivity to cancer cells comprising a phosphomevalonate kinase (PMVK) protein expression or activity inhibitor as an active ingredient.

In order to achieve the above another object, the present invention provides a method of providing information necessary for diagnosing radiation-resistant cancer, the method comprises: (1) measuring mRNA expression level of PMVK gene or expression level of PMVK protein from a sample isolated from a cancer patient; (2) comparing the mRNA expression level of the PMVK gene or the expression level of the PMVK protein with a control sample; and (3) determining that it is radiation-resistant cancer when the mRNA expression level of the PMVK gene or the expression level of the PMVK protein is higher than that of the control sample.

Also, the present invention provides a method of providing information necessary for predicting prognosis of radiation therapy in a cancer patient, the method comprises: (1) measuring mRNA expression level of PMVK gene or expression level of PMVK protein from a sample isolated from a cancer patient; (2) comparing the mRNA expression level of the PMVK gene or the expression level of the PMVK protein with a control sample; and (3) determining that the prognosis of radiation therapy is poor when the mRNA expression level of the PMVK gene or the expression level of the PMVK protein is higher than that of the control sample.

In order to achieve the above another object, the present invention provides a method of screening a radiation sensitivity enhancer for cancer cells, the method comprises: (1) contacting a cancer cell with a test substance; (2) measuring expression or activity level of a PMVK protein in the cancer cells contacted with the test substance; and (3) selecting a test substance having a reduced expression or activity level of the PMVK protein compared to a control sample.

In addition, the present invention provides a use of a PMVK protein or a gene encoding the same as a biomarker for diagnosing radiation-resistant cancer.

In addition, the present invention provides a use of an agent capable of measuring the expression level of PMVK for diagnosing radiation-resistant cancer.

Furthermore, the present invention provides a use of a PMVK protein or a gene encoding the same as a biomarker for predicting the prognosis of radiation therapy in a cancer patient.

In addition, the present invention provides a use of an agent capable of measuring the expression level of PMVK for predicting the prognosis of radiation therapy in a cancer patient.

In addition, the present invention provides a use of a PMVK protein expression or activity inhibitor to manufacture a medicament for enhancing the radiation sensitivity to cancer cells.

Advantageous Effects

The present invention relates to a biomarker composition for diagnosing radiation-resistant cancer or a biomarker composition the prognosis of radiation therapy, comprising a phosphomevalonate kinase (PMVK) protein or a gene encoding the same as an active ingredient, and has identified the PMVK gene that can enhance the sensitivity of radiation in A549 cells which are a human lung cancer cell, established stable cell lines for A549 cells and pancreatic cancer cells Miapaca-2 cells using shRNA, and verified the increased effect of enhancing radiation sensitivity through cell and animal experiments, and further the contribution of the over-expression of PMVK to radiation resistance through clinical data analysis. Thus, since PMVK can be used as a therapeutic target gene for overcoming radiation resistance in human lung and pancreatic cancer, gene therapy or other drugs that increase the sensitivity of radiation to target PMVK can be developed to increase the effect of the radiation therapy more and more.

BEST MODE

Hereinafter, the present invention will be described in more detail.

The present invention provides a biomarker composition for diagnosing radiation-resistant cancer comprising a phosphomevalonate kinase (PMVK) protein or a gene encoding the same as an active ingredient.

Preferably, the biomarker composition may further comprise a conventionally known radiation-resistant biomarker, and the conventionally known radiation-resistant biomarkers include CD133, CD144 and CD24, but they are not limited thereto.

As used herein, the term "diagnosis" includes determining the susceptibility of an object to a particular disease or disorder, determining whether an object currently has a particular disease or disorder, determining the prognosis of the object having has a particular disease or disorder, or therametrics (e.g., monitoring the status of the object to provide information regarding the therapeutic efficacy).

Also, the present invention provides a composition for diagnosing radiation-resistant cancer comprising an agent capable of measuring the expression level of PMVK as an active ingredient.

Specifically, the agent capable of measuring expression level of PMVK may be a primer or a probe specifically binding to the PMVK gene, an antibody, a peptide, an aptamer or a compound specifically binding to the PMVK protein, but it is not limited thereto.

The cancer may be lung cancer or pancreatic cancer, but it is not limited thereto.

In addition, the present invention provides a kit for diagnosing radiation-resistant cancer comprising the composition.

Furthermore, the present invention provides a biomarker composition for predicting the prognosis of radiation therapy in a cancer patient comprising a phosphomevalonate kinase (PMVK) protein or a gene encoding the same as an active ingredient.

As used herein, the term "prognosis prediction" refers to an act of predicting the course and result of a disease beforehand. More specifically, the course of the disease after treatment may vary depending on the physiological or environmental condition of the patient, and it can be interpreted as meaning all the actions that predict the course of the disease after treatment considering the condition of the patient as a whole.

For the purpose of the present invention, the prognosis prediction can be interpreted as predicting the disease-free survival rate or the survival rate of the cancer patient by predicting the course of the disease and the complete treatment after the radiation therapy of a cancer patient. For example, predicting a "good prognosis" indicates a high level of disease-free survival or survival rate in cancer patients after radiation therapy, which implies that cancer patients are more likely to be treated, and the prediction of "poor prognosis" indicates a low level of disease-free survival or survival rate in cancer patients after radiation therapy, which implies that the cancer is likely to recur from cancer patients or the patients is likely to die due to cancer.

In addition, the present invention provides a composition for predicting the prognosis of radiation therapy in a cancer patient comprising an agent capable of measuring the expression level of PMVK as an active ingredient.

At this time, the agent capable of measuring expression level of PMVK may be a primer or a probe specifically binding to the PMVK gene, an antibody, a peptide, an aptamer or a compound specifically binding to the PMVK protein.

The cancer may be lung cancer or pancreatic cancer, but it is not limited thereto.

In addition, the present invention provides a kit for predicting the prognosis of radiation therapy in a cancer patient comprising the composition.

As used herein, the term "primer" refers to a nucleic acid sequence having a short free 3'-hydroxyl group, which can form base pairs with a complementary template, and short nucleic acid serving as a starting point for template strand replication. The primers can initiate DNA synthesis in the presence of reagents for polymerization (i.e., DNA polymerase or reverse transcriptase) and four different nucleoside triphosphates under appropriate buffer solutions and temperatures. The PCR conditions and the lengths of the sense and antisense primers can be appropriately selected according to techniques known in the art.

As used herein, the term "probe" refers to a nucleic acid fragment such as RNA or DNA corresponding to a few base or several hundreds of bases that can specifically bind to an mRNA and the presence or absence of a specific mRNA, expression level can be confirmed by labeling. The probe may be prepared in the form of an oligonucleotide probe, a single strand DNA probe, a double strand DNA probe, or an RNA probe. The selection of suitable probes and hybridization conditions can be appropriately selected according to techniques known in the art.

As used herein, the term "antibody" is well known in the art and means a specific immunoglobulin as directed against an antigenic site. An antibody in the present invention means an antibody which specifically binds to PMVK of the present invention, and an antibody can be produced according to a conventional method in the art. The form of the antibody includes polyclonal or monoclonal antibodies, including all immunoglobulin antibodies. The antibody refers to a complete form having two full-length light chains and two full-length heavy chains. The antibody also includes a special antibody such as a humanized antibody.

As used herein, the term "peptide" has a high binding capacity to a target material and does not cause denaturation during thermal/chemical treatment. Also, because of its small size, it can be used as a fusion protein by attaching it to other proteins. It can be used as a diagnostic kit and a drug delivery material because it can be specifically attached to a polymer protein chain.

As used herein, the term "aptamer" refers to a polynucleotide composed of a specific type of single-stranded nucleic acid (DNA, RNA or modified nucleic acid) having a stable tertiary structure by itself and having the property for capable of binding to a target molecule with high affinity and specificity. As described above, since the aptamer is composed of a polynucleotide which can specifically bind to an antigenic substance like an antibody and is more stable than the protein, has a simple structure, and is easy to synthesize and thus can be used instead of an antibody.

In addition, the kit of the present invention may include an antibody specifically binding to a marker component, a secondary antibody conjugate conjugated with a marker that develops color by reaction with a substrate a secondary antibody conjugate conjugated with a marker to be colored by reaction with a substrate, a chromogenic substrate solution to develop color reaction with the marker, a washing solution and an enzymatic reaction stop solution a substrate solution to develop a color to react with a marker, washing solution, and It may include an enzyme reaction stop solution, etc., and may be manufactured in a number of separate packaging or compartments containing reagent components used.

In addition, the present invention provides a pharmaceutical composition for enhancing radiation sensitivity to cancer cells comprising a phosphomevalonate kinase (PMVK) protein expression or activity inhibitor as an active ingredient.

Specifically, the PMVK expression inhibitor may be any one selected from the group consisting of antisense nucleotides, small interfering RNA (siRNA) and short hairpin RNA (shRNA) that complementarily bind to mRNA of the PMVK gene, and the PMVK activity inhibitor may be any one selected from the group consisting of low molecular compounds, peptides, peptide mimetics, aptamers, antibodies and natural products that specifically bind to the PMVK protein, but it is not limited thereto.

In this case, the cancer cells may be lung cancer cells or pancreatic cancer cells.

The pharmaceutical composition of the present invention may contain a chemical substance, a nucleotide, an antisense, a siRNA oligonucleotide and a natural product extract as an active ingredient. The pharmaceutical composition or combination preparation of the present invention may be prepared by using pharmaceutically acceptable and physiologically acceptable adjuvants in addition to the active ingredients, and examples of the adjuvants include solubilizers such as excipients, disintegrants, sweeteners, binders, coating agents, swelling agents, lubricants, slip modifiers or flavors. The pharmaceutical composition of the present invention may be formulated into a pharmaceutical composition containing at least one pharmaceutically acceptable carrier in addition to the active ingredient for administration. Acceptable pharmaceutical carriers for compositions which are formulated into liquid solutions include sterile saline, sterile water, Ringer's solution, buffered saline, albumin injection solution, dextrose solution, maltodextrin solution, glycerol, ethanol and its mixture of at least one, which is suitable for sterilization and in vivo, and if necessary, other conventional additives such as an antioxidant, a buffer and a bacteriostatic agent may be added. In addition, diluents, dispersants, surfactants, binders, and lubricants can be additionally added to formulate into injectable solutions such as aqueous solutions, suspensions, emulsions and the like, pills, capsules, granules or tablets.

The pharmaceutical preparation form of the pharmaceutical composition of the present invention may be granules, powders, coated tablets, tablets, capsules, suppositories, syrups, juices, suspensions, emulsions, drips or injectable liquids and a sustained release formulation of the active compound, and the like. The pharmaceutical compositions of the present invention may be administered in a conventional manner via Intravenous, intraarterial, intraperitoneal, intramuscular, intraarterial, intraperitoneal, intrasternal, percutaneous, nasal, inhaled, topical, rectal, oral, intraocular or intradermal routes. The effective amount of the active ingredient of the pharmaceutical composition of the present invention means the amount required for preventing or treating the disease. Accordingly, the present invention can be adjusted according to various factors such as the particular type of the disease, the severity of the disease, the kind and amount of the active ingredient and other ingredients contained in the composition, the type of formulation and the patient's age, body weight, general health status, sex and diet, time of administration, route of administration and secretion rate of the composition, duration of treatment, concurrent medication, and the like. It is not limited thereto, but for example, in the case of an adult, when administered once to several times a day, the composition of the present invention may be administered at a dose of 0.1 ng/kg to 10 g/kg of compound, 0.1 ng/kg to 10 g/kg of In polypeptide, protein or antibody, 0.01 ng/kg to 10 g/kg of antisense nucleotide, siRNA, shRNAi and miRNA.

Moreover, the present invention provides a method of providing information necessary for diagnosing radiation-resistant cancer, the method comprises: (1) measuring mRNA expression level of PMVK gene or expression level of PMVK protein from a sample isolated from a cancer patient; (2) comparing the mRNA expression level of the PMVK gene or the expression level of the PMVK protein with a control sample; and (3) determining that it is radiation-resistant cancer when the mRNA expression level of the PMVK gene or the expression level of the PMVK protein is higher than that of the control sample.

In addition, the present invention provides a method of providing information necessary for predicting prognosis of radiation therapy in a cancer patient, the method comprises: (1) measuring mRNA expression level of PMVK gene or expression level of PMVK protein from a sample isolated from a cancer patient; (2) comparing the mRNA expression level of the PMVK gene or the expression level of the PMVK protein with a control sample; and (3) determining that the prognosis of radiation therapy is poor when the mRNA expression level of the PMVK gene or the expression level of the PMVK protein is higher than that of the control sample.

At this time, the cancer may be lung cancer or pancreatic cancer, but it is not limited thereto.

As used herein, the term "sample isolated from a cancer patient" includes a sample such as tissue, cell, whole blood, serum, plasma, saliva, sputum, cerebrospinal fluid, or urine, which is different from the control group in the expression level of the PMVK gene or the PMVK protein, a biomarker for diagnosing radiation-resistant cancer, but it is not limited thereto.

Specifically, the method of measuring the mRNA expression level may be RT-PCR, competitive RT-PCR, real-time RT-PCR, RNase protection assay, Northern blotting and DNA chips, but it is not limited thereto.

Specifically, the method of measuring the protein expression level may be Western blot, enzyme linked immunosorbent assay (ELISA), radioimmunoassay (RIA), radioimmunodiffusion, Ouchterlony immunodiffusion, rocket, immunoelectrophoresis, tissue immunostaining, immunoprecipitation assays, complement fixation assays, FACS and protein chips, but it is not limited thereto.

In the present invention, the term "radiation-resistant cancer diagnosis" is intended to confirm whether cancer cells are resistant or susceptible to radiation, for predicting radiation therapy strategy and radiation therapy effect in cancer patients.

In addition, the present invention provides a method of screening a radiation sensitivity enhancer for cancer cells, the method comprises: (1) contacting a cancer cell with a test substance; (2) measuring expression or activity level of a PMVK protein in the cancer cells contacted with the test substance; and (3) selecting a test substance having a reduced expression or activity level of the PMVK protein compared to a control sample.

The term "test substance" used in referring to the screening method of the present invention means an unknown candidate substance used in screening to examine whether it affects the expression amount of a gene or the expression or activity of a protein. The samples include chemicals, nucleotides, antisense-RNA, siRNA (small interference RNA) and natural extracts, but it is not limited thereto.

In addition, the present invention provides a use of a PMVK protein or a gene encoding the same as a biomarker for diagnosing radiation-resistant cancer.

In addition, the present invention provides a use of an agent capable of measuring the expression level of PMVK for diagnosing radiation-resistant cancer.

In addition, the present invention provides a use of a PMVK protein or a gene encoding the same as a biomarker for predicting the prognosis of radiation therapy in a cancer patient.

In addition, the present invention provides a use of an agent capable of measuring the expression level of a PMVK protein for predicting the prognosis of radiation therapy in a cancer patient.

In addition, the present invention provides a use of a PMVK protein expression or activity inhibitor to manufacture a medicament for enhancing radiation sensitivity to cancer cells.

Hereinafter, the present invention will be described in detail with reference to the following examples. It will be apparent to those skilled in the art that the following examples are intended to illustrate the contents of the present invention, but the scope of the present invention is not limited to the following examples.

Example 1

Confirmation of Radiation Sensitivity Enhancing Gene PMVK Through Screening of Human Kinases siRNA Library 1. Experimental Method Three screenings of genes that enhance sensitivity to radiation using Dharmacon siGENOME® SMARTpool® siRNA library (718 human protein kinase: G-003505) in A549 human lung cancer cells (purchased from ATCC) were performed.

Specifically, 0.5 μl of Lipofectamine® RNAiMAX Reagent (Invitrogen: 13778-150) was added to a 96-well plate in which siRNA was present at a concentration of 50 nM each, and A549 cells were seeded at $0.3 \times 10^4$ cells and incubated for 24 hours. The cultured cells were treated with 8 Gy of radiation using a 6-MV photon beam linear accelerator. On the 9th day after radiation treatment, the cell viability was analyzed three times through the CCK-8 assay and as a result, information was obtained that the PMVK gene is a candidate gene related to sensitivity to radiation. In addition, whether the protein is knocked down or not by Dharmacon siGENOME® SMARTpool® human PMVK siRNA present in the siRNA library (Target Sequences: UUUAUCCGCUCCAGACUUU (SEQ ID NO: 1), CGAGAACCAUGGAGUUGAA (SEQ ID NO: 2), AAUGUGGCCUGGACAACUU (SEQ ID NO: 3), GGUGAGUGACACGAGA); Cat #M-006782-01) was confirmed by performing Western blotting using PMVK antibody after that 1 μl of Lipofectamine® RNAiMAX Reagent (Invitrogen: 13778-150) was added to a 24 well plate containing PMVK siRNA at a concentration of 50 nM and A549 cells were seeded at $3 \times 10^4$ cells, incubated for 24 hours and protein was extracted from one well. After the remaining 24 wells were treated with 5 Gy and 10 Gy of radiation, CCK-8 assay was performed to confirm the survival rate of the cells.

2. Experimental Results

Figure 1:
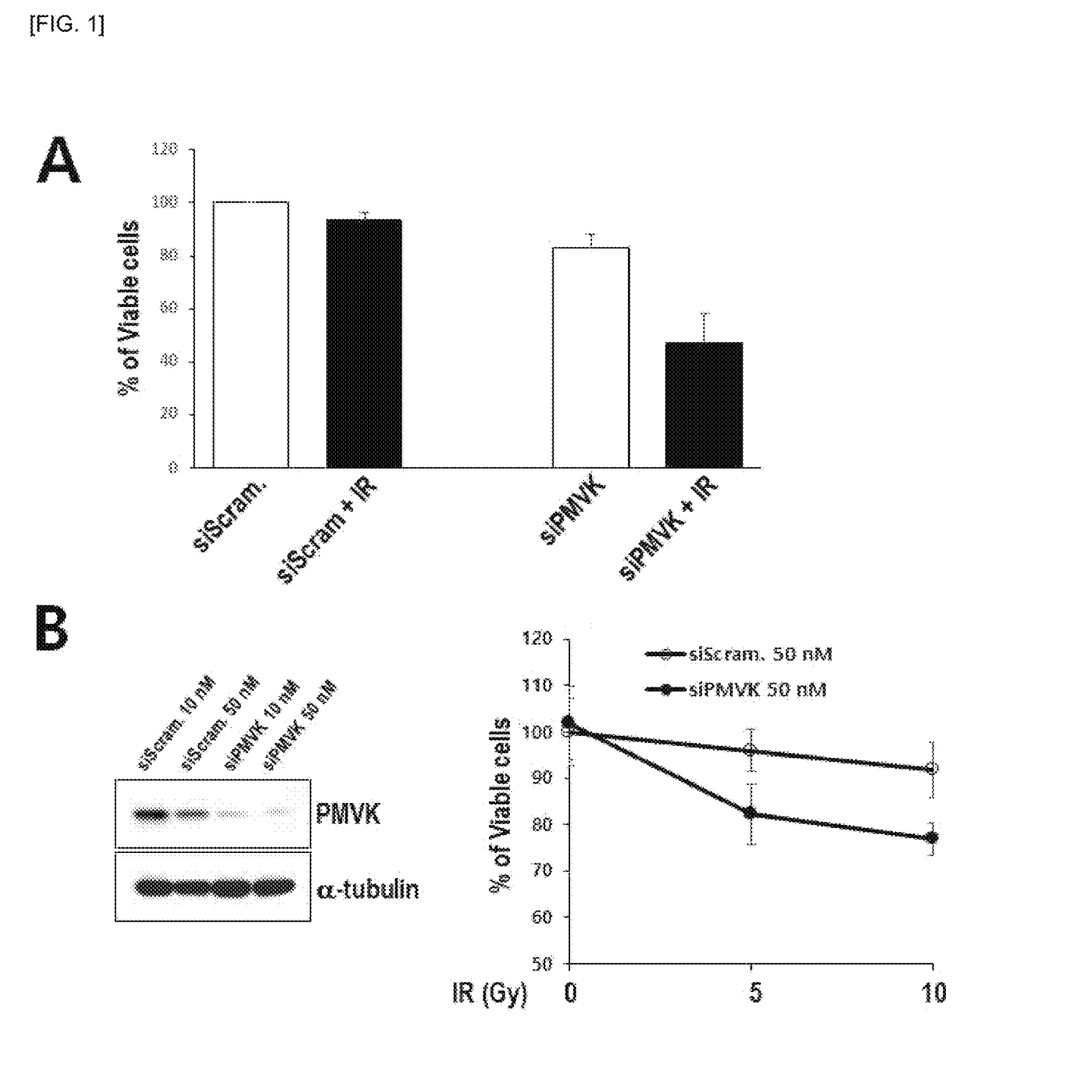
FIG. 1 shows results of confirming the radiation sensitivity enhancing gene PMVK through human kinase siRNA library screening in one example of the present invention (A: a result of confirming radiation sensitivity enhancing gene PMVK by screening of human lung kinase siRNA library in A549 human lung cancer cell line, B: a result of confirming cell viability reduction upon the inhibition of PMVK protein expression by PMVK siRNA and radiation treatment).

As a result, as shown in FIG. 1A, it was observed that the cell survival rate was significantly reduced when the radiation was treated after transfection of PMVK siRNA than when siScramble (control, target sequences): UGGUUUACAUGUCGACUAA (SEQ ID NO: 5), UGGUUUACAUGUUGUGUGA (SEQ ID NO: 6)), UGGUUUACAUGUUUUCUGA (SEQ ID NO: 7), UGGUUUACAUGUUUUCCUA (SEQ ID NO: 8); Dharmacon, Non-Targeting pool, Cat #D-001810-10-20) were treated with radiation.

In addition, as shown in FIG. 1B, as a result of Western blotting, it was confirmed that the protein was knocked down by PMVK siRNA, and it was confirmed once again that the survival rate of the cell was decreased during radiation treatment.

Therefore, based on these results, it was determined that the reduction of PMVK expression would be involved in the enhancement of radiation sensitivity.

Example 2

PMVK shRNA Stable Cell Line Construction and Colony Formation Survival Analysis 1. Experimental Method For stable knock-down of PMVK, PMVK shRNA stable cell lines were constructed in A549 (lung cancer) and Miapaca-2 (pancreatic cancer; purchased from ATCC) cells. Specifically, Dharmacon PMVK shRNA (Clone ID: V3LHS_350080, mature antisense: TCTGACTCAGCATCGTCCA; SEQ ID NO: 9) was transfected to A549 cells and Miapaca-2 cells by FuGENE® transfection reagent (Roche: REF 04 709 713 001), then 4 μg/ml of puromycin was selected for 15 days to construct A549/shPMVK cells (2 clones; A549/shPMVK #1 and A549/shPMVK #3) and Miapaca-2/The shPMVK cell line (3 clones; Mia/shPMVK #1, Mia/shPMVK #2, Mia/shPMVK #3) and the expression level of PMVK protein was confirmed through Western blotting.

In addition, in order to examine whether the A549/shPMVK stable cell line and the Miapaca-2/shPMVK stable cell line constructed as described above enhance the sensitivity of radiation, a cell colony forming assay was performed after treatment with radiation to both cell lines. That is, after seeding 200 or 2000 cells in a 6-well plate, radiation was treated with 0, 2, 4, 5, 8, and 10 Gy and it was quantitatively analyzed by staining colonies with 20% methanol and 0.5% crystal violet after 7 to 14 days and counting the number.

2. Experimental Results

Figure 2:
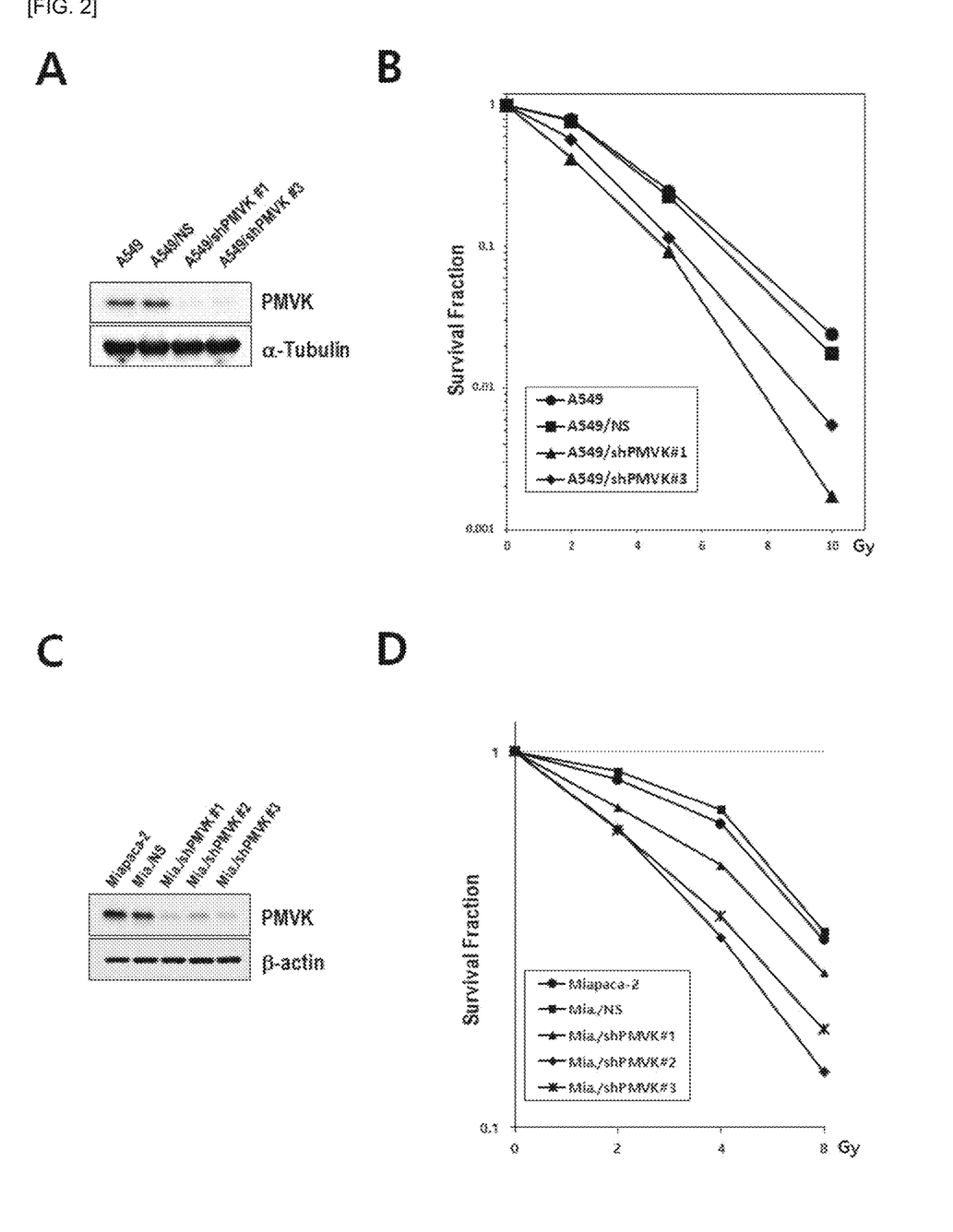
FIG. 2 shows results of constructing a PMVK shRNA stable cell line, and treating the constructed cells with radiation to perform colony formation survival assay in one example of the present invention (A: a result of confirming the PMVK protein expression inhibitory effect in A549/shPMVK stable cell line, B: a result of confirming the effect of radiation on colony formation in A549/shPMVK stable cell line, C: a result of confirming the PMVK protein expression inhibitory effect in Miapaca-2/shPMVK stable cell line, D: a result of confirming the effect of radiation on colony formation in Miapaca-2/shPMVK stable cell line).

As a result, as shown in FIG. 2A and FIG. 2C, compared to the parent cell (A549, Miapaca-2) and non-silencing control (A549/NS, Miapaca-2/NS), it was confirmed that the PMVK protein expression was significantly reduced in the newly constructed A549/shPMVK stable cell line and Miapaca-2/shPMVK stable cell line.

In addition, as shown in FIG. 2B and FIG. 2D, as a result of the cell colony formation survival assay for the A549/shPMVK stable cell line and the Miapaca-2/shPMVK stable cell line constructed as described above, it was found that the colony formation was significantly reduced.

Example 3

Evaluation of Efficacy Against Radiation in A549/shPMVK Cell Transplant Mouse Model 1. Experimental Method For in vivo experiments, cancer tissues were formed by transplanting $1 \times 10^6$ of A549, A549/NS, A549/shPMVK #1 (stable A549 cell line transfected with shRNA of SEQ ID NO: 9) and A549/shPMVK #3 (stable A549 cell line transfected with shRNA of SEQ ID NO: 9) transfected with shRNA of 1) cells to the right calf of the nude mouse, respectively. Thereafter, 5 Gy of radiation was irradiated twice every two days, and the change of the cancer growth was observed for 30 days by measuring the size using a caliper 3 times a week and at the same time, the body weight of the mouse was also measured and cancer tissues were extracted on Day 30 to check size and weight. At this time, the cancer size was calculated as described in <Equation 1> below.

$$\text{Tumor volume} = [\text{length} \times \text{width}^2] \times 0.5 \qquad \text{[Equation 1]}$$

2. Experimental Results

Figure 3A:
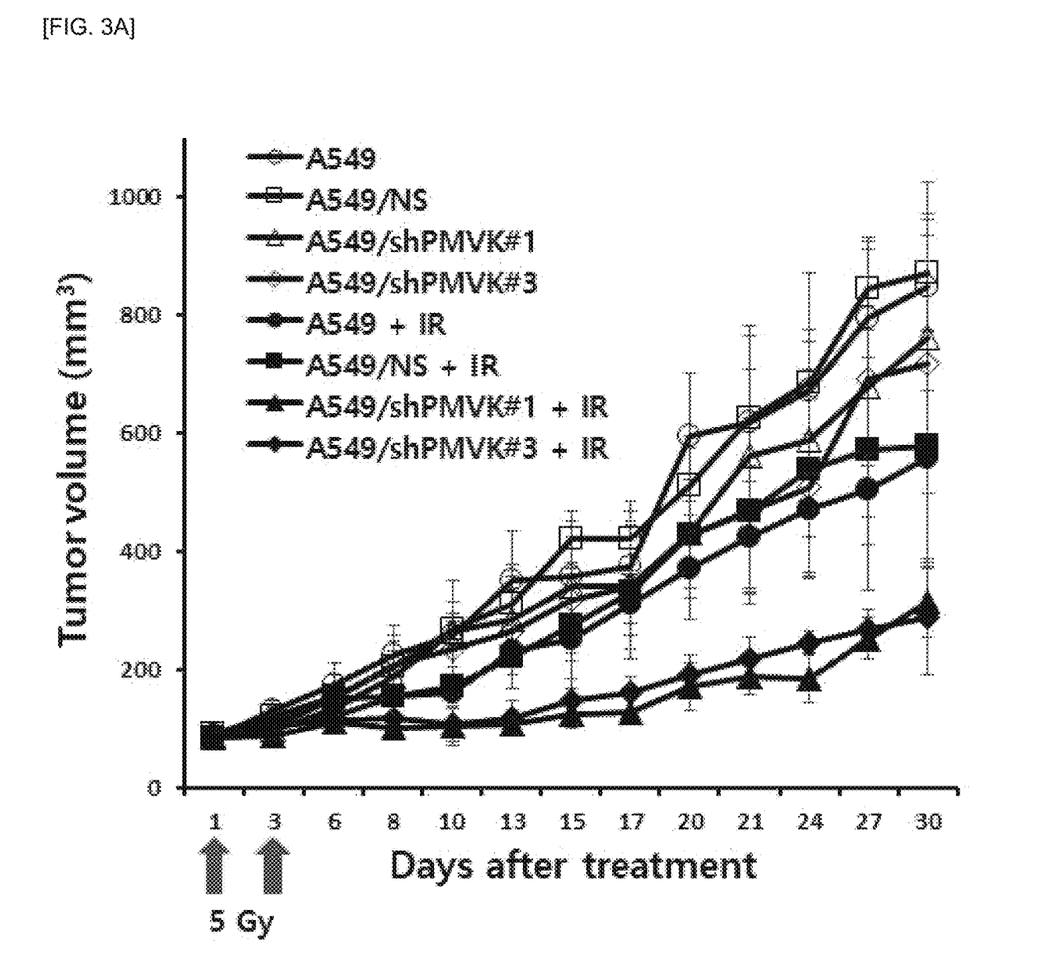
FIGS. 3A-3D show results of the evaluating the efficacy against the radiation of A549/shPMVK cell transplant mouse model in one example of the present invention (3A: comparison of cancer growth by volume, 3B: comparison of weight of mouse, 3C: comparison of the size of the extracted cancer, 3D: comparison of the weight of the extracted cancer).
Figure 3B:
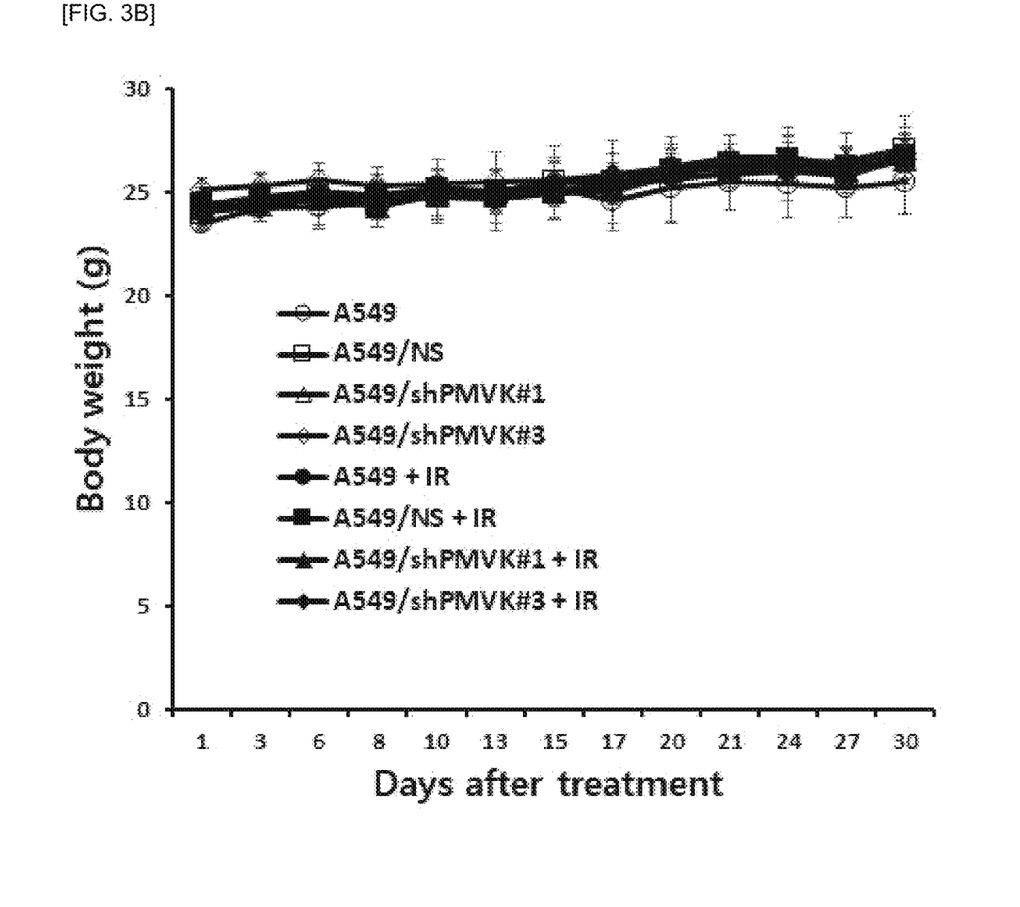
Figure 3C:
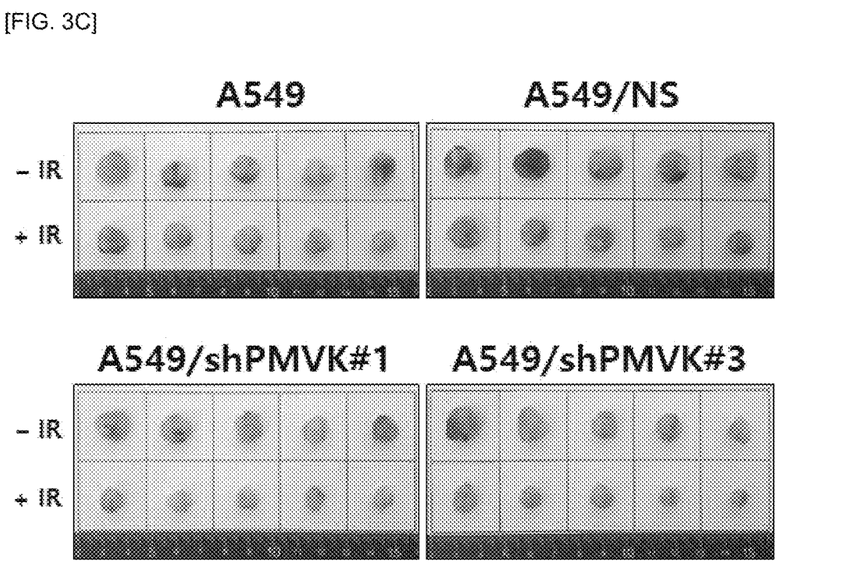
Figure 3D:
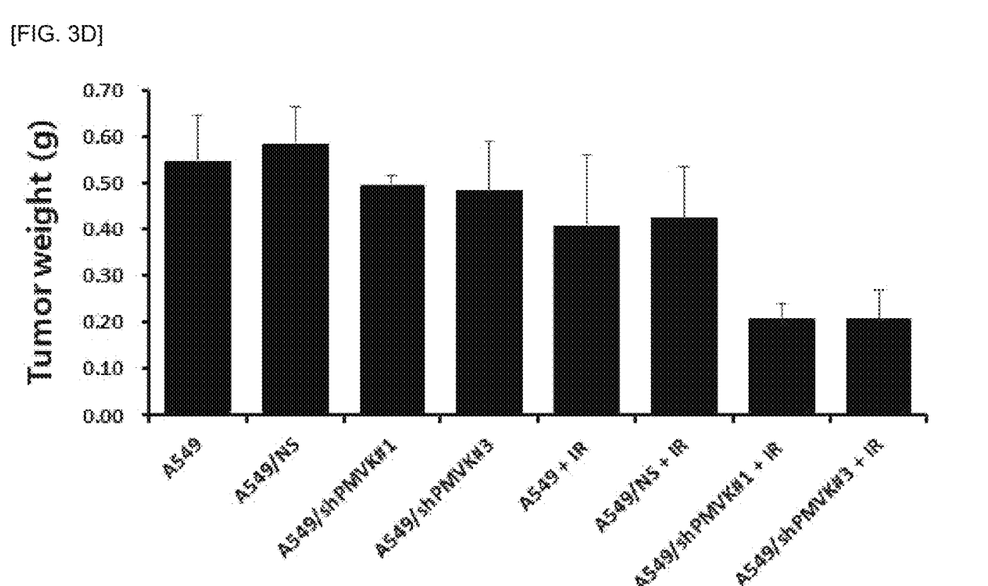

As a result, as shown in FIGS. 3A-3D, it was confirmed that cancer growth was significantly inhibited when the radiation was treated with A549/shPMVK #1 and #3 than that of A549 or A549/NS with radiation (FIG. 3A and FIG. 3C), where no change in body weight was observed in the mouse (FIG. 3B). It was confirmed that even when cancer weight was measured by extracting cancer tissue from all mice at the end of the experiment, the weight of cancer tissue treated with radiation in A549/shPMVK #1 and #3 was the lowest (FIG. 3D).

Example 4

Clinical Genome Data Analysis

1. Experimental Method

To investigate the relationship between PMVK expression and survival in patients, the survival rate was investigated through analysis of previously reported genome data for lung cancer patients (GSE68465; NCBI. GEO, n=442). After dividing into the radiation treated patient group (n=65) and the non-radiated patient group (n=364), the patient survival rate was investigated according to the expression of PMVK.

2. Experimental Results

Figure 4:
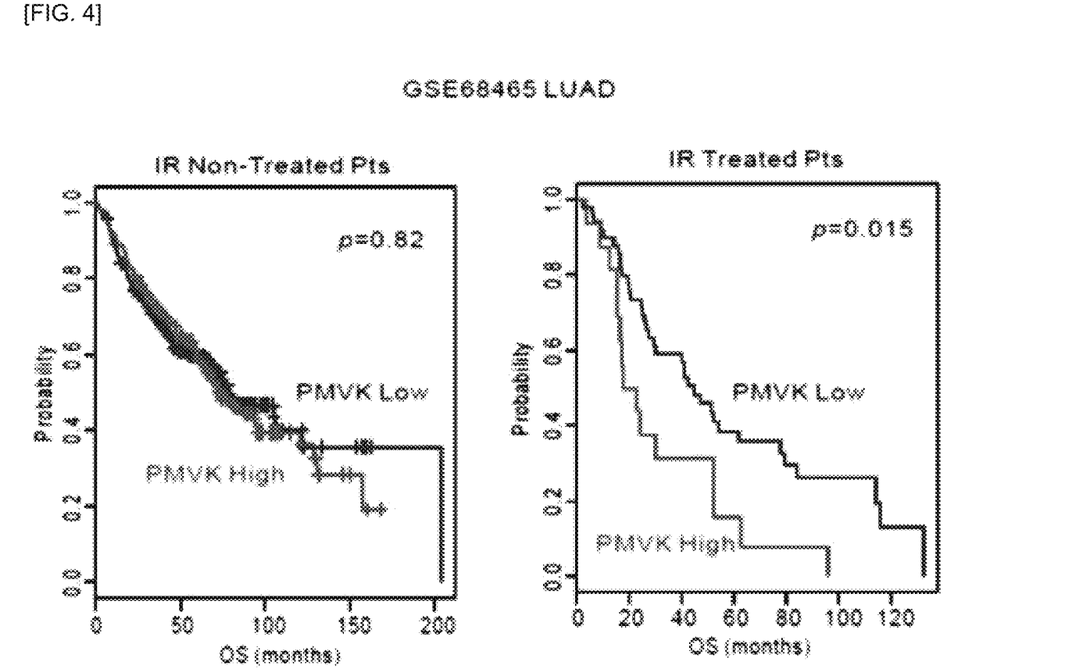
FIG. 4 shows results of clinical genomic data analysis according to PMVK expression during radiation treatment to a lung cancer patient group in one example of the present invention.

As a result, as shown in FIG. 4, it was found that in the radiation-treated patient group, the survival rate was poor in the patient group with high expression of PMVK, while the patient's survival rate was improved as a result of radiation treatment in the patient group with low expression of PMVK. However, it was confirmed that the patient group without radiation treatment did not affect the survival rate regardless of whether PMVK was expressed or not.

Through these results, it was confirmed that the expression of PMVK and the survival rate of the patient during radiation treatment are closely related, and that the inhibition of PMVK can help improve the survival rate of the patient during radiation treatment.

Example 5

Efficacy Evaluation Against Radiation in Miapaca-2/shPMVK Cell Transplant Mouse Model 1. Experimental Method For in vivo experiments, cancer tissues were formed by transplanting $2 \times 10^6$ of Miapaca-2, Miapaca-2/NS, Miapaca-2/shPMVK #2 (stable Miapaca-2 cell line transfected with shRNA of SEQ ID NO: 9) and Miapaca-2/shPMVK #3 (stable Miapaca-2 cell line transfected with shRNA of SEQ ID NO: 9) transfected with shRNA of 1) cells to the right calf of the nude mouse, respectively. Thereafter, 2 Gy of radiation was irradiated three times every two days, and the change of the cancer growth was observed for 30 days by measuring the size using a caliper 3 times a week and at the same time, the body weight of the mouse was also measured. At this time, the cancer size was calculated as described in <Equation 1> below.

$$\text{Tumor volume} = [\text{length} \times \text{width}^2] \times 0.5 \quad [\text{Equation 1}]$$

2. Experimental Results

Figure 5:
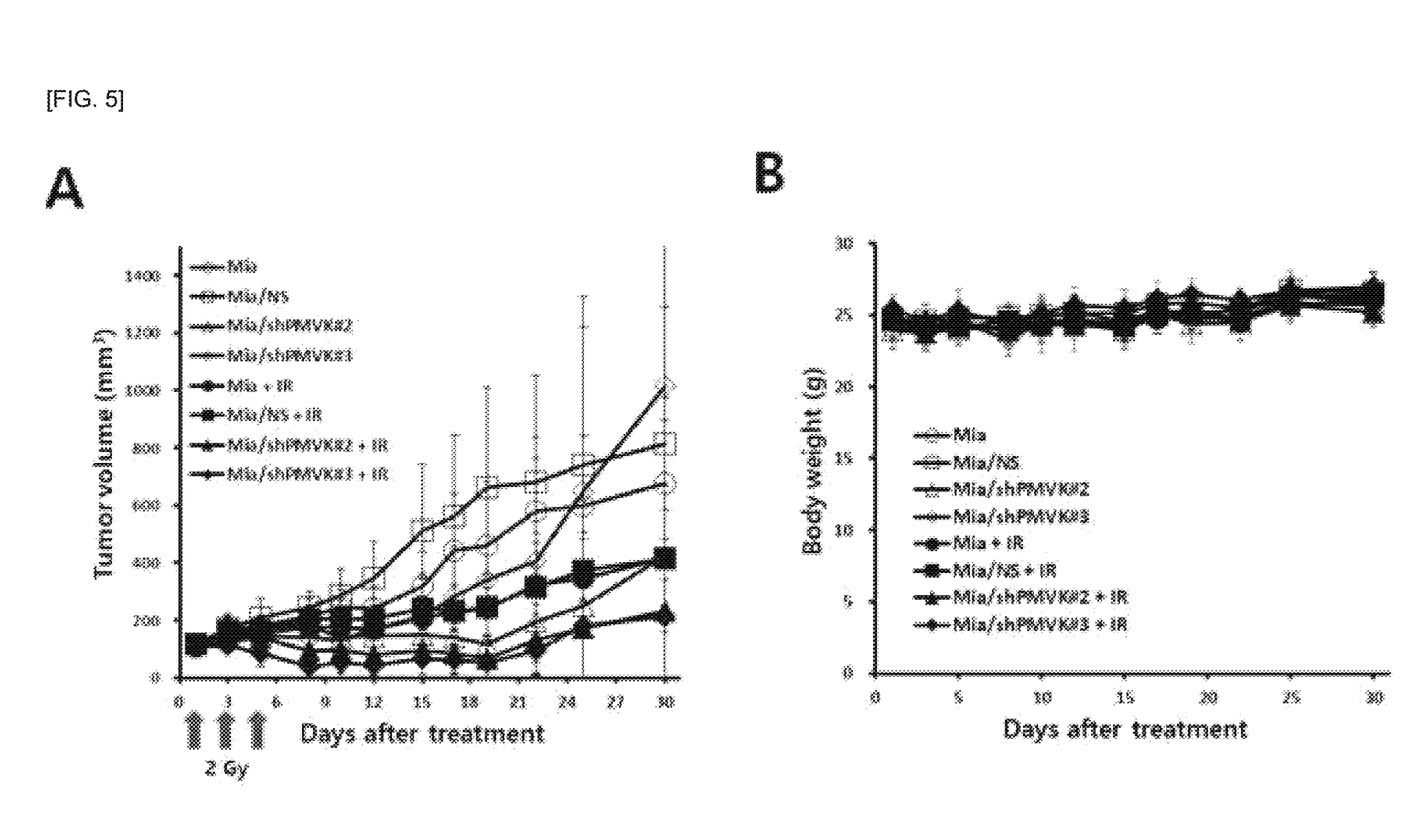
FIG. 5 shows results of evaluating the efficacy against the radiation in a Miapaca-2/shPMVK cell transplant mouse model in one example of the present invention.

As a result, as shown in FIG. 5, it was confirmed that the cancer growth was significantly inhibited when the radiation was treated with Miapaca-2/shPMVK #2 and #3 than that when the radiation was treated with Miapaca-2 or Miapaca-2/NS. (FIG. 5A), at this time, no change was exhibited in body weight of the mouse (FIG. 5B).

While the present invention has been particularly described with reference to specific embodiments thereof, it is apparent that this specific description is only a preferred embodiment and that the scope of the present invention is not limited thereby to those skilled in the art. That is, the practical scope of the present invention is defined by the appended claims and their equivalents.

The invention claimed is:

1. A method for enhancing radiation sensitivity to cancer cells comprising a step of administering to a subject in need thereof a pharmaceutical composition comprising a phosphomevalonate kinase (PMVK) protein expression inhibitor as an active ingredient,
   wherein the PMVK protein expression inhibitor is a small interfering RNA (siRNA) selected from the group consisting of SEQ ID NOS: 1-3 or a short hairpin RNA (shRNA) of SEQ ID NO: 9.

2. The method of claim 1, wherein the cancer cells are lung cancer cells or pancreatic cancer cells.

* * * * *

SEQUENCE LISTING

```
<160> NUMBER OF SEQ ID NOS: 9

<210> SEQ ID NO 1
<211> LENGTH: 19
<212> TYPE: DNA
<213> ORGANISM: Artificial Sequence
<220> FEATURE:
<223> OTHER INFORMATION: PMVK siRNA

<400> SEQUENCE: 1
uuuauccgcu ccagacuuu                                              19

<210> SEQ ID NO 2
<211> LENGTH: 19
<212> TYPE: DNA
<213> ORGANISM: Artificial Sequence
<220> FEATURE:
<223> OTHER INFORMATION: PMVK siRNA

<400> SEQUENCE: 2
cgagaaccau ggaguugaa                                              19

<210> SEQ ID NO 3
<211> LENGTH: 19
<212> TYPE: DNA
<213> ORGANISM: Artificial Sequence
<220> FEATURE:
<223> OTHER INFORMATION: PMVK siRNA

<400> SEQUENCE: 3
```

-continued aauguggccu ggacaacuu                                              19

<210> SEQ ID NO 4
<211> LENGTH: 19
<212> TYPE: DNA
<213> ORGANISM: Artificial Sequence
<220> FEATURE:
<223> OTHER INFORMATION: PMVK siRNA

<400> SEQUENCE: 4
ggugagugac acacggaga                                              19

<210> SEQ ID NO 5
<211> LENGTH: 19
<212> TYPE: DNA
<213> ORGANISM: Artificial Sequence
<220> FEATURE:
<223> OTHER INFORMATION: siScramble

<400> SEQUENCE: 5
ugguuuacau gucgacuaa                                              19

<210> SEQ ID NO 6
<211> LENGTH: 19
<212> TYPE: DNA
<213> ORGANISM: Artificial Sequence
<220> FEATURE:
<223> OTHER INFORMATION: siScramble

<400> SEQUENCE: 6
ugguuuacau guuguguga                                              19

<210> SEQ ID NO 7
<211> LENGTH: 19
<212> TYPE: DNA
<213> ORGANISM: Artificial Sequence
<220> FEATURE:
<223> OTHER INFORMATION: siScramble

<400> SEQUENCE: 7
ugguuuacau guuuucuga                                              19

<210> SEQ ID NO 8
<211> LENGTH: 19
<212> TYPE: DNA
<213> ORGANISM: Artificial Sequence
<220> FEATURE:
<223> OTHER INFORMATION: siScramble

<400> SEQUENCE: 8
ugguuuacau guuuuccua                                              19

<210> SEQ ID NO 9
<211> LENGTH: 19
<212> TYPE: DNA
<213> ORGANISM: Artificial Sequence
<220> FEATURE:
<223> OTHER INFORMATION: Mature antisense

<400> SEQUENCE: 9
tctgactcag catcgtcca                                              19